United States Patent [19]

Toei et al.

[11] Patent Number: 4,877,522
[45] Date of Patent: Oct. 31, 1989

[54] LIQUID SUPPLY APPARATUS

[75] Inventors: Junichi Toei, Sagamihara; Nobuyuki Baba, Yamato, both of Japan

[73] Assignee: Tosho Corporation, Shin-nanyo, Japan

[21] Appl. No.: 319,874

[22] Filed: Mar. 1, 1989

Related U.S. Application Data

[63] Continuation of Ser. No. 191,239, May 6, 1988, abandoned.

[30] Foreign Application Priority Data

May 11, 1987 [JP] Japan ................................ 62-112274

[51] Int. Cl.⁴ .............................................. B01D 15/08
[52] U.S. Cl. ................................ 210/198.2; 210/96.1; 210/101; 366/152; 366/160
[58] Field of Search .................... 210/96.1, 101, 198.2; 366/152, 160, 177, 182

[56] References Cited

U.S. PATENT DOCUMENTS

| | | | |
|---|---|---|---|
| 2,513,562 | 7/1950 | Holuba | 366/152 |
| 3,794,301 | 2/1974 | Simmonds | 366/152 |
| 3,843,099 | 10/1974 | Duncan | 366/152 |
| 4,116,046 | 9/1978 | Stein | 210/198.2 |
| 4,116,834 | 9/1978 | King | 210/101 |
| 4,217,217 | 8/1980 | Kay | 210/96.1 |
| 4,311,586 | 1/1982 | Baldwin | 210/101 |
| 4,403,866 | 9/1983 | Falcoff | 366/152 |
| 4,427,298 | 1/1984 | Fahy | 366/160 |
| 4,433,917 | 2/1984 | Mendel | 366/152 |
| 4,465,593 | 8/1984 | Wemhoff | 210/96.1 |
| 4,474,476 | 10/1984 | Thomsen | 366/152 |
| 4,475,821 | 10/1984 | Koch | 366/160 |
| 4,478,713 | 10/1984 | Girot | 210/101 |
| 4,621,927 | 11/1986 | Hiroi | 366/160 |
| 4,728,434 | 3/1988 | Trafford | 366/160 |

FOREIGN PATENT DOCUMENTS

| | | | |
|---|---|---|---|
| 685716 | 5/1964 | Canada | 366/152 |
| 60222139 | 11/1985 | Japan | 366/152 |

*Primary Examiner*—Ernest G. Therkorn
*Attorney, Agent, or Firm*—Oblon, Spivak, McClelland, Maier & Neustadt

[57] ABSTRACT

A liquid supply apparatus comprising a mixing tank provided with a stirring means for stirring a liquid mixture, an electrode for measuring the hydrogen ion concentration of the liquid mixture, a plurality of supply liquid tanks for storing different supply liquids, a liquid supply section for supplying the supply liquids to the mixing tank, a supply control section for controlling the amounts of the supply liquids to be supplied at the liquid supply section based on a difference between a preliminary memorized initially the value and a measured value signaled from the electrode and on the amounts of the supply liquids supplied to the mixing tank, conduits connecting the supply liquid tanks and the liquid supply section and a conduit connecting the liquid supply section and the mixing tank.

3 Claims, 2 Drawing Sheets

LIQUID SUPPLY APPARATUS

This application is a continuation of application Ser. No. 191,239, filed on May 6, 1988, now abandoned.

BACKGROUND OF THE INVENTION

1. Field of the Invention

The present invention relates to a liquid supply apparatus useful for preparing an eluting solution to be used for e.g. liquid chromatography or a reactant solution to be used for a reaction.

2. Discussion of Background

In liquid chromatography wherein a certain component in a sample solution is separated by a difference in the affinity to gel, the separation is usually substantially affected by a small change in e.g. the pH, the concentration of salts or the concentration of organic solvents in the eluting solution. Therefore, it is necessary to precisely adjust the composition of the eluting solution.

Also in the field of an analysis such as a colorimetric analysis, it is required to prepare a reactant solution with extremely high precision to control the analytical reaction precisely or to improve the reproducibility of the analysis.

However, the conventional methods for preparation of these solutions are very time-consuming and lack in precision. An example of such operational procedure will be given below.

When 1 liter of a solution comprising a 0.1M sodium dihydrogenphosphate/disodium hydrogenphosphate buffer solution (pH 5.5) and 20% methanol is to be prepared by using a 1M sodium dihydrogenphosphate ($NaH_2PO_4$) solution (solution A), a 1M disodium hydrogenphosphate ($Na_2PO_4$) solution (solution B), 100% methanol and distilled water, firstly an operation of alternately adding solution A and solution B followed by stirring is repeated while watching a hydrogen ion concentration meter (a pH meter) until the hydrogen ion concentration (pH) reaches 5.5. This operation is continued until the total amount of the two solutions reaches 100 ml. Then, the electrode is taken out from the solution, and 200 ml of methanol is measured by a measuring cylinder and added to the solution. Further, 700 ml of distilled water is measured by a measuring cylinder and added to the solution. This is a common procedure for the preparation of such a solution.

In such a procedure, it takes a long time to adjust the hydrogen ion concentration in the solution to a predetermined level, as mentioned above, and it also requires a substantial labor to precisely adjust the amount of the buffer solution to 100 ml. Further, the procedure involves a number of measuring operations, whereby a number of measuring equipments are required, and the preparation and after-treatment of such equipments are time- and labor-consuming.

In order to overcome these drawbacks, it has been proposed to adjust the composition of a solution by means of a conventional supply apparatus. However, with a usual supply apparatus, the hydrogen ion concentration of the solution can not be measured. Thus, such a proposal has a serious drawback that the hydrogen ion concentration of the adjusted solution can not be made constant.

SUMMARY OF THE INVENTION

It is an object of the present invention to provide a liquid supply apparatus whereby a sample solution having an accurate hydrogen ion concentration and composition can be prepared simply and precisely as compared with the conventional methods.

The present invention provides a liquid supply apparatus comprising a mixing tank provided with a stirring means for stirring a liquid mixture, an electrode for measuring the hydrogen ion concentration of the liquid mixture, a plurality of supply liquid tanks for storing different supply liquids, a liquid supply section for supplying the supply liquids to the mixing tank, a supply control section for controlling the amounts of the supply liquids to be supplied at the liquid supply section based on a difference between a preliminarily memorized predetermined value and a measured value signaled from the electrode and on the amounts of the supply liquids supplied to the mixing tank, conduits connecting the supply liquid tanks and the liquid supply section and a conduit connecting the liquid supply section and the mixing tank.

DETAILED DESCRIPTION OF THE PREFERRED EMBODIMENTS

Figure 1:
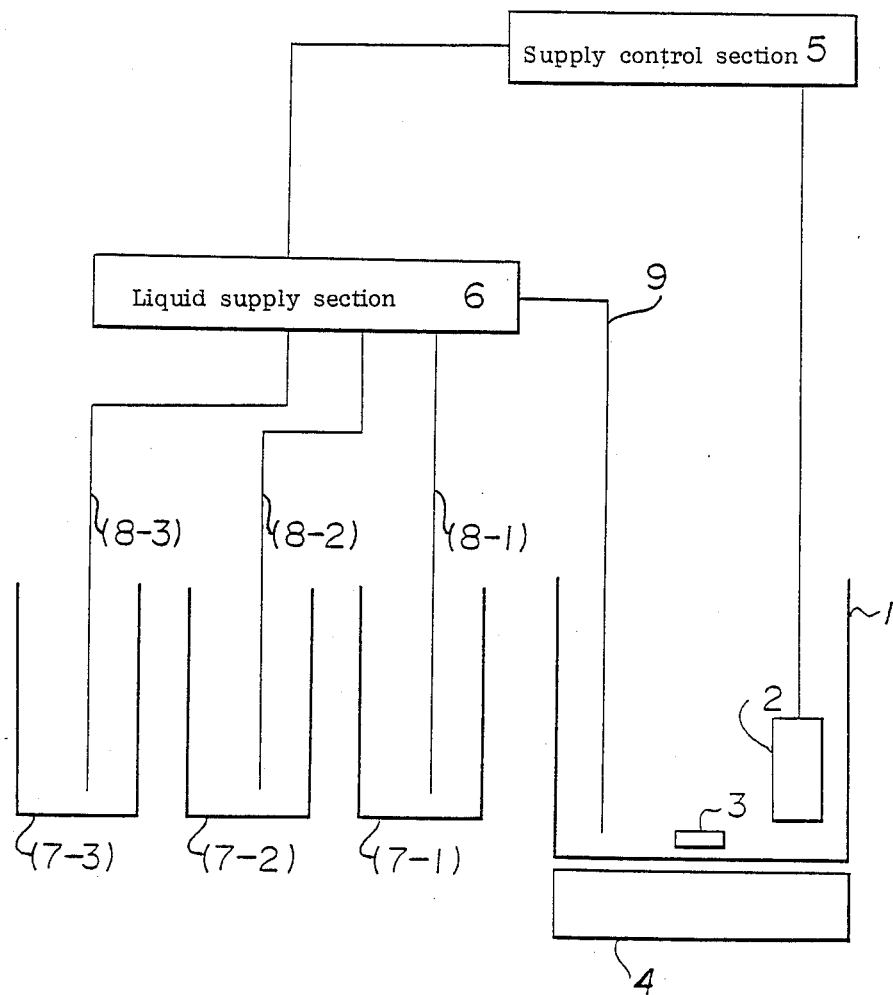
FIG. 1 is a diagrammatic view illustrating an embodiment of the apparatus of the present invention.

Now, the present invention will be described in detail.

In order to obtain a solution having a predetermined hydrogen ion concentration from a plurality of solutions, the present invention is designed to control, when supply liquids (the solutions) are supplied from the supply liquid tanks via the liquid supply section to the mixing tank provided with an electrode for measuring the hydrogen ion concentration, the supply amounts in response to signals from the electrode received by the supply control section to bring the hydrogen ion concentration to the predetermined level.

With respect to the mixing tank of the present invention, there is no particular restriction so long as it is capable of storing the supplied and mixed solution. It is provided with a stirring means for stirring the solution. The stirring means may be of any type so long as it is capable of stirring the solution in the mixing tank and may be the one utilizing a magnetic stirrer or the one utilizing rotary plates or rotary vanes.

As the electrode for measuring the hydrogen ion concentration, an electrode commonly used in a hydrogen ion concentration meter (a pH meter) may be used without any problem. Such an electrode may simply be disposed in the mixing tank so that it is immersed in the solution for a prescribed period of time. It may be designed so that after the measurement of the hydrogen ion concentration, the electrode portion is automatically cleaned and retracted from the mixing tank.

The supply control section is necessary to receive a signal of data measured by the hydrogen ion concentration meter and give an instruction to the liquid supply section as to which supply liquid should be supplied next. This supply control section memorizes the supply liquids in the supply liquid tanks and the predetermined level (the predetermined value) of the hydrogen ion concentration in the liquid mixture. It instructs and controls the liquid supply section to adjust the hydrogen ion concentration in the liquid mixture in response to the measured value of the hydrogen ion concentration of the liquid mixture in the mixing tank. It is designed to be operated by a computer program for the control. Namely, when the measured value of the hydrogen ion concentration in the liquid mixture is lower than the predetermined value, the supply control section recognizes the difference between the predetermined value and the measured value and automatically instructs the liquid supply section to supply a liquid having a higher hydrogen ion concentration from an appropriate supply liquid tank, so that the hydrogen ion concentration in the liquid mixture is adjusted to the predetermined value by the addition of the liquid. Likewise, when the predetermined value and the measured value are in a reversed relation, the supply control section operates to add a supply liquid having a lower hydrogen ion concentration.

The liquid supply section of the present invention is a section for supplying the supply liquids to the mixing tank, and a liquid supply device commonly employed in liquid chromatography such as a syringe type or a rotary type liquid supply device may suitably be employed depending upon the particular purpose. The liquid supply section is electrically connected with the above described supply control section to supply the optimum amounts of the supply liquids from the respective supply liquid tanks to the mixing tank in response to signals from the above described supply control section. This liquid supply section may be composed of a single liquid supply section to which pipe lines from the plurality of supply liquid tanks are connected, or it may be composed of a plurality of liquid supply sections connected to the respective supply liquid tanks. Either structure may be selected for use depending upon the particular purpose. However, the former structure is preferred from the viewpoint of the simplicity of the apparatus. However, in the case of a supply pipe line intended for supplying a large amount of a liquid such as pure water for dilution, an independent supply system for exclusive use may be employed. The conduit from the liquid supply section to the mixing tank may be provided in the same concept.

With respect to the supply liquid tanks, there is no particular restriction so long as they are made of a material inert to supply liquids used.

The conduits connecting the supply liquid tanks to the liquid supply section and the liquid supply section to the mixing tank may suitably be made of stainless steel pipes or Teflon ® pipes commonly employed in liquid chromatography.

Now, the present invention will be described with reference to FIG. 1 which shows an embodiment of the present invention.

This apparatus comprises a mixing tank 1 provided with an electrode 2 for measuring the hydrogen ion concentration and a stirring means comprising a magnetic stirrer 3 and a motor driving device 4 to rotate the stirrer 3, a plurality of supply liquid tanks 7 storing different liquids, a liquid supply section 6 for introducing the supply liquids from the supply liquid tanks 7 to the mixing tank 1, a supply control section 5 for controlling the supply amounts in response to the signals from the electrode 2, and conduits 8 and 9 connecting the supply liquid tanks 7 to the liquid supply section 6 and the liquid supply section 6 to the mixing tank 1.

In this apparatus, supply liquids are introduced from a plurality of supply liquid tanks (7-1, 7-2, ... ) by a plurality of pipe lines (8-1, 8-2, ... ) to the liquid supply section 6, and the supply from the liquid supply section 6 to the mixing tank 1 is conducted by a single pipe line 9. Between the respective pipe lines (8-1, 8-2, ... ) and the liquid supply section 6, valves or magnetic valves (not shown) are provided as means to prevent inflow from other conduits.

The operation will be described with respect to an example wherein a solution (A) having a hydrogen ion concentration (m) is put in a supply liquid tank (7-1), a solution (B) having a hydrogen ion concentration (n) is put in a supply liquid tank (7-2), and a mixed solution having a hydrogen ion concentration of x and a total amount of the solution of y ml is to be prepared. The hydrogen ion concentrations of the solutions (A) and (B) are assumed to have a relation of $m > n$.

Firstly, data such as theoretically calculated amounts of the solutions (A) and (B) to be added and the predetermined hydrogen ion concentration (x) of the mixed solution, are input in the supply control section 5. The amounts to be added are usually adjusted so that they constitute from 80 to 90% of the total amount y ml of the mixed solution.

An appropriate amount of the solution (A) is introduced via the liquid supply section 6 to the mixing tank, and the hydrogen ion concentration of the solution in the mixing tank is measured by the electrode. This measured value is designated as z. The supply control section 5 judges that the measured value (z) is higher than the predetermined value (x) in the hydrogen ion concentration and instructs to supply the solution (B) to the mixing tank 1. Then, the supply control section 5 reads the supply amounts a ml and b ml of the solutions (A) and (B), respectively, when the predetermined value (x) and the measured value (z) have become to be equal, and it calculates the supply amounts of the rest of the solutions (A) and (B) so that the total amount of the mixed solution is adjusted to y while maintaining the predetermined value (x). Based on the results of this calculation, the supply of the respective solutions (A) and (B) is instructed to the liquid supply section 6, whereby the supply to the mixing tank is conducted to complete the supply treatment. If the solution (B) is supplied first, the supply treatment will be conducted by an operation based on a judgement reverse to the above.

As in the above case, the supply amount may be calculated at every supply operation of each liquid. However, it is also possible that the respective solutions are supplied in small portions and each time the hydrogen ion concentration is measured to judge the difference from the predetermined value, and this operation is repeated until the measured value (z) agrees to the predetermined value (x), whereby the total supply amounts up to this point are calculated, and the subsequent operation may be conducted in the same manner as described above to prepare a mixed solution.

Figure 2:
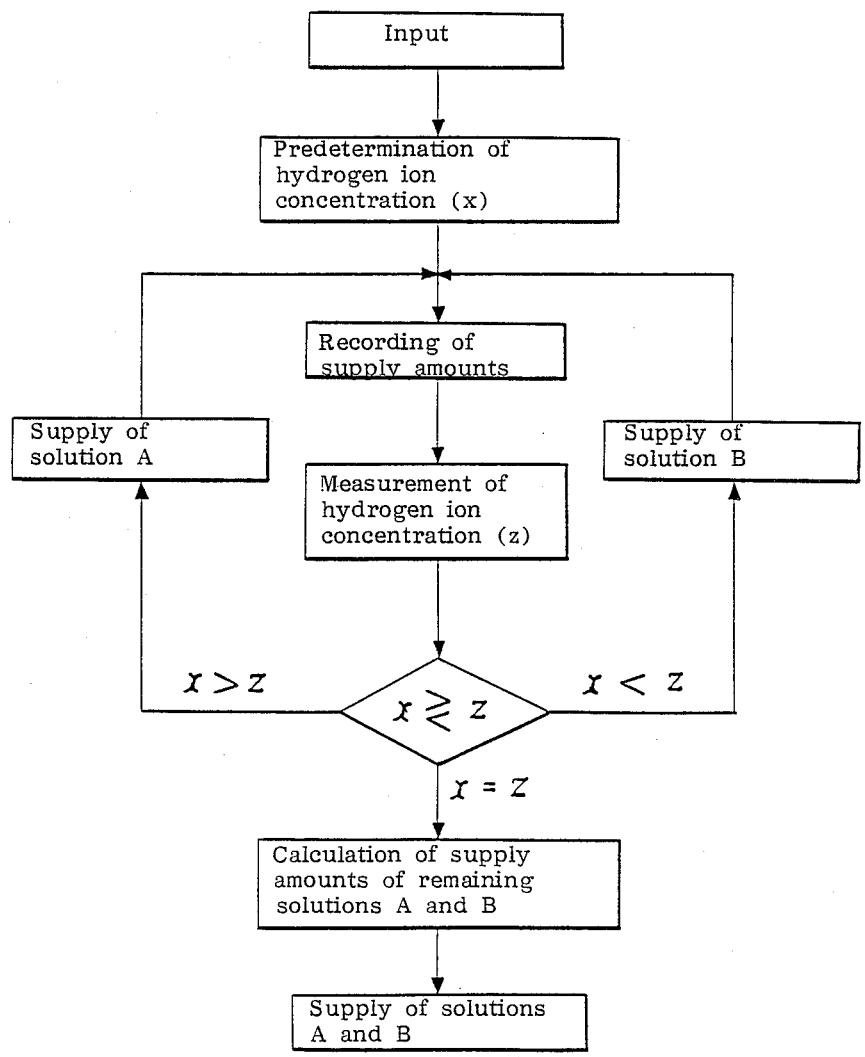
FIG. 2 is a flow chart illustrating the control at the supply control section of the apparatus of the present invention.

FIG. 2 shows an example of a flow chart of the control at the supply control section comprising a series of these operations.

It should be apparent from the foregoing description that according to the apparatus of the present invention, the hydrogen ion concentration in the mixed solution can be adjusted to an optional level, whereby it is possible to prepare a solution having a predetermined hydrogen ion concentration readily and simply and yet with high precision, and it is possible to uniformly mix solutions in simple operation.

What is claimed is:

1. A liquid supply apparatus for providing a precisely predetermined volume of liquid mixture having a precisely predetermined hydrogen ion concentration for liquid chromatography, comprising:

a mixing tank;

stirring means for stirring a liquid mixture in said mixing tank;

electrode means for measuring a hydrogen ion concentration of said liquid mixture in said mixing tank;

a plurality of supply liquid tanks for storing different supply liquids;

liquid supply section means for supplying controlled volumes of said supply liquids to said mixing tank; and supply control section means for controlling said liquid supply section means, including:

(a) means for calculating first volumes of said supply liquids such that a liquid mixture having a first volume less than said predetermined volume will have a hydrogen ion concentration equal to said predetermined hydrogen ion concentration, (b) means for controlling said liquid supply section means for supplying said first volumes of said supply liquids to said mixing tank until a measured hydrogen ion concentration of said liquid mixture equals said predetermined hydrogen ion concentration of said liquid mixture;

(c) means for determining the total volume of said supply liquids supplied to said mixing tank when the measured hydrogen ion concentration of said liquid mixture equals said predetermined hydrogen ion concentration of said liquid mixture;

(d) means for calculating additional volumes of said supply liquids such that a liquid mixture having said total volume plus said additional volumes of said supply liquid will have said predetermined volume; and (e) means for controlling said liquid supply section means for supplying said additional volumes of said supply liquids to said supply mixture in said mixing tank until the volume of the liquid mixture in said mixing tank equals said predetermined volume, while maintaining said measured hydrogen ion concentration of the mixed liquid in said mixing tank at said predetermined hydrogen ion concentration.

2. The apparatus of claim 1 wherein said first volume of said liquid mixture is between 80% and 90% of said predetermined volume.

3. The apparatus of claim 1 wherein said supply control section means comprises a computer.

* * * * *